United States Patent
Goto et al.

(10) Patent No.: US 10,518,018 B2
(45) Date of Patent: Dec. 31, 2019

(54) BLOOD PURIFICATION SYSTEM

(71) Applicant: Nikkiso Company Limited, Tokyo (JP)

(72) Inventors: Hitoshi Goto, Shizuoka (JP); Tomoya Murakami, Shizuoka (JP); Masahiro Toyoda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 49 days.

(21) Appl. No.: 15/631,332

(22) Filed: Jun. 23, 2017

(65) Prior Publication Data

US 2017/0281849 A1 Oct. 5, 2017

Related U.S. Application Data

(63) Continuation of application No. PCT/JP2015/085913, filed on Dec. 24, 2015.

(30) Foreign Application Priority Data

Dec. 26, 2014 (JP) ................................. 2014-265057

(51) Int. Cl.
  *A61M 1/36* (2006.01)
  *A61L 2/00* (2006.01)
(52) U.S. Cl.
  CPC ............... *A61M 1/36* (2013.01); *A61L 2/0011* (2013.01); *A61M 1/3607* (2014.02); *A61M 1/3639* (2013.01)
(58) Field of Classification Search
  CPC ............ A61M 1/36; A61M 1/14; A61M 1/34; A61M 1/3601; A61M 1/3639;
  (Continued)

(56) References Cited

U.S. PATENT DOCUMENTS

2011/0066043 A1 * 3/2011 Banet .................. A61B 5/022
                                                        600/485

FOREIGN PATENT DOCUMENTS

JP   2003-010319 A   1/2003
JP   2007-000238 A   1/2007
(Continued)

OTHER PUBLICATIONS

International Search Report from the Japanese Patent Office for Application No. PCT/JP2015/085913, dated Feb. 9, 2016.
(Continued)

*Primary Examiner* — Philip R Wiest
(74) *Attorney, Agent, or Firm* — Young Basile Hanlon & MacFarlane, P.C.

(57) ABSTRACT

A blood purification system that is capable of notifying any changes in the patient's condition on the basis of noninvasive vital sings of the patient that are observed during the blood purification treatment. An external information-processing apparatus includes an external input device into which a vital sign detected by a detecting device is inputtable in real time; a checking device capable of checking whether or not the vital sign inputted in real time into the external input device satisfies a predetermined condition; and an external output device capable of outputting, if it is determined by the checking device that the vital sign satisfies the predetermined condition, a result of the checking or checked information including the vital sign leading to the result of the checking to a blood purification apparatus. The checked information outputted from the external output device is displayable on a display included in the blood purification apparatus.

20 Claims, 8 Drawing Sheets

(58) Field of Classification Search
CPC .. A61M 2205/3561; A61M 2205/3576; A61M 2205/502; A61M 2205/52; A61M 2230/04; A61M 1/3607; A61L 2/0011; A61L 2/0017
See application file for complete search history.

(56) References Cited

FOREIGN PATENT DOCUMENTS

| | | |
|---|---|---|
| JP | 2012-000291 A | 1/2012 |
| JP | 2014-000307 A | 1/2014 |
| JP | 2014-004194 A | 1/2014 |

OTHER PUBLICATIONS

Extended European Search Report for Application No. 15873120.8 dated Jun. 1, 2018.

\* cited by examiner

*RoC : Rate of change
*BP  : Blood Pressure
*WFD : Waveform details
*WFC : Waveform comparison

[Fig 6]

*BP : Blood Pressure

[Fig 7]

*BP : Blood Pressure

*tgt Kt/v : Target Kt/V
*WFD : Waveform details
*WFC : Waveform comparison

BLOOD PURIFICATION SYSTEM

FIELD

The present invention relates to a blood purification system including a blood purification apparatus and an external information-processing apparatus, the blood purification apparatus being capable of performing blood purification treatment in which blood of a patient that is under extracorporeal circulation is purified, the external information-processing apparatus being capable of receiving and monitoring, in real time, vital signs detected by a detecting device.

BACKGROUND

In general, dialysis treatment is performed by using a dialysis treatment apparatus including a blood circuit for extracorporeally circulating the blood of a patient, a dialyzer connected to a halfway point of the blood circuit, a peristaltic blood pump, and a dialysis-apparatus body capable of performing ultrafiltration while performing hemodialysis treatment in which dialysate is introduced into or delivered from the dialyzer. Typically, dialysis treatment performed with such a dialysis treatment apparatus continues for about four hours and is given every other day. Accordingly, impurities accumulated in two days need to be removed in about four hours. Therefore, the hemodynamics of the patient during the treatment changes significantly. Particularly, it is important to efficiently and assuredly prevent the decrease in blood pressure caused by the removal of excessive water (ultrafiltration).

To solve the above problem, some apparatuses have hitherto been proposed in which the hematocrit value (the volume fraction of blood-cell components in the blood) of the blood of the patient during dialysis treatment is detected, and the rate of change in the circulating blood volume ($\Delta BV$) of the patient is calculated from the detected hematocrit value and is monitored. According to another proposal (see PTL 1, for example), not only information, such as the rate of change in the circulating blood volume ($\Delta BV$), obtained from the blood that is under extracorporeal circulation but also noninvasive vital signs of the patient observed during the blood purification treatment are detected successively, and the detected vital signs are displayed, whereby any changes in the condition of the patient (particularly, a decrease in blood pressure) can be notified efficiently and assuredly.

CITATION LIST

Patent Literature

PTL 1: Japanese Unexamined Patent Application Publication No. 2007-238

SUMMARY

In the above known technique, changes in the patient's condition can be notified efficiently and assuredly by successively detecting and displaying noninvasive vital signs of the patient during the blood purification treatment. However, if vital signs are detected and displayed in real time, a huge amount of information is obtained during the dialysis treatment. Hence, the information-processing capacity of the blood purification apparatus (the dialysis treatment apparatus) needs to be increased (high-spec hardware is required). Such a situation leads to a problem of an increase in the manufacturing cost.

Even if noninvasive vital signs of the patient during the blood purification treatment can be displayed in real time, it is not necessarily required to display normal vital signs in real time for every blood purification apparatus because, in a typical case where a large number (20 to 30, for example) of dialysis treatment apparatuses are operated simultaneously in one facility, it is difficult to assign one person in the medical profession exclusively to the monitoring of one dialysis treatment apparatus for over the entire period of time taken for the treatment.

In view of the above circumstances, the present teachings provide a blood purification system that is capable of efficiently and assuredly notifying any changes in the patient's condition on the basis of noninvasive vital sings of the patient that are observed during the blood purification treatment, with a blood purification apparatus manufacturable at a reduced cost.

According to the teachings herein, a blood purification system includes a blood purification apparatus capable of performing blood purification treatment in which blood of a patient that is extracorporeally circulated is purified, the apparatus including a display capable of displaying information on the blood purification treatment in real time; a detecting device capable of detecting in real time a noninvasive vital sign of the patient during the blood purification treatment; and an external information-processing apparatus capable of receiving and monitoring in real time the vital sign detected by the detecting device. The external information-processing apparatus includes an external input device into which the vital sign detected by the detecting device is inputtable in real time; a checking device capable of checking whether or not the vital sign inputted in real time into the external input device satisfies a predetermined condition; and an external output device capable of outputting, if it is determined by the checking device that the vital sign satisfies the predetermined condition, a result of the checking or checked information including the vital sign leading to the result of the checking to the blood purification apparatus. The checked information outputted from the external output device is displayable on a display included in the blood purification apparatus.

According to the teachings, the blood purification system according to the teachings herein, the checking device is capable of checking whether or not the vital sign inputted in real time is abnormal, and the result of the checking that is determined to be abnormal or the checked information including the vital sign leading to the result of the checking is outputted from the external output device.

According to the teachings, the blood purification system according to the teachings herein, the external information-processing apparatus includes a storage device capable of memorizing and storing the vital sign inputted in real time into the external input device.

According to the teachings, the blood purification system according to the teachings herein, the external information-processing apparatus includes an external display capable of displaying the vital sign inputted in real time into the external input device.

According to the teachings, the blood purification system according to the teachings herein, the blood purification apparatus includes a browser capable of requesting information displayed on the external display and that allows the information to be displayed on the display in accordance with the request.

According to the teachings, the blood purification system according to the teachings herein, the noninvasive vital sign detectable by the detecting device includes at least one of electrocardiogram, pulse wave, heart rate, pulse rate, body temperature, oxygen saturation, and respiration rate of the patient.

According to the teachings, the blood purification system according to the teachings herein, the external information-processing apparatus is a central monitoring apparatus capable of transmitting a condition for or information on the blood purification treatment to the blood purification apparatus or a bed-side terminal provided near the patient during the blood purification treatment.

According to the teachings herein, the external information-processing apparatus includes the external input device into which a vital sign detected by the detecting device is inputtable in real time, the checking device capable of checking whether or not the vital sign inputted in real time into the external input device satisfies the predetermined condition, and the external output device capable of outputting, if it is determined by the checking device that the vital sign satisfies the predetermined condition, the result of the checking or the checked information including the vital sign leading to the result of the checking to the blood purification apparatus. The checked information outputted from the external output device is displayable on the display of the blood purification apparatus. Therefore, while the manufacturing cost of the blood purification apparatus is suppressed, any changes in the patient's condition can be efficiently and assuredly notified on the basis of noninvasive vital signs of the patient that are observed during the blood purification treatment.

According to the teachings herein, the checking device is capable of checking whether or not the vital sign inputted in real time is abnormal. Furthermore, the result of the checking that is determined to be abnormal or the checked information including the vital sign leading to the result of the checking is outputted from the external output device. Therefore, while the manufacturing cost of the blood purification apparatus is suppressed, any abnormalities can be efficiently and assuredly notified on the basis of noninvasive vital signs of the patient that are observed during the blood purification treatment.

According to the teachings herein, the external information-processing apparatus includes the storage device capable of memorizing and storing the vital sign inputted in real time into the external input device. Therefore, the vital sign that is inputted in real time into the external input device during the treatment can be referred to whenever necessary.

According to the teachings herein, the external information-processing apparatus further includes the external display capable of displaying the vital sign inputted in real time into the external input device. Therefore, information including the vital sign to be displayed can be processed by the external information-processing apparatus.

According to the teachings herein, the blood purification apparatus includes the browser capable of requesting the information displayed on the external display and that allows the information to be displayed on the display in accordance with the request. Therefore, the blood purification apparatus does not need to perform arithmetic processes and the like that are necessary for displaying the vital sign in real time.

According to the teachings herein, the noninvasive vital sign detectable by the detecting device includes at least one of the electrocardiogram, pulse wave, heart rate, pulse rate, body temperature, oxygen saturation, and respiration rate of the patient. Therefore, changes in the patient's condition can be efficiently and assuredly notified on the basis of any of the electrocardiogram, pulse wave, heart rate, pulse rate, body temperature, oxygen saturation, and respiration rate of the patient.

According to the teachings herein, the external information-processing apparatus is a central monitoring apparatus capable of transmitting conditions for or information on the blood purification treatment to the blood purification apparatus or a bed-side terminal provided near the patient during the blood purification treatment. Therefore, any central monitoring apparatus or any bed-side terminal included in any known blood purification system can be used.

DETAILED DESCRIPTION

An embodiment of the present invention will now be described specifically with reference to the drawings.

Figure 1:
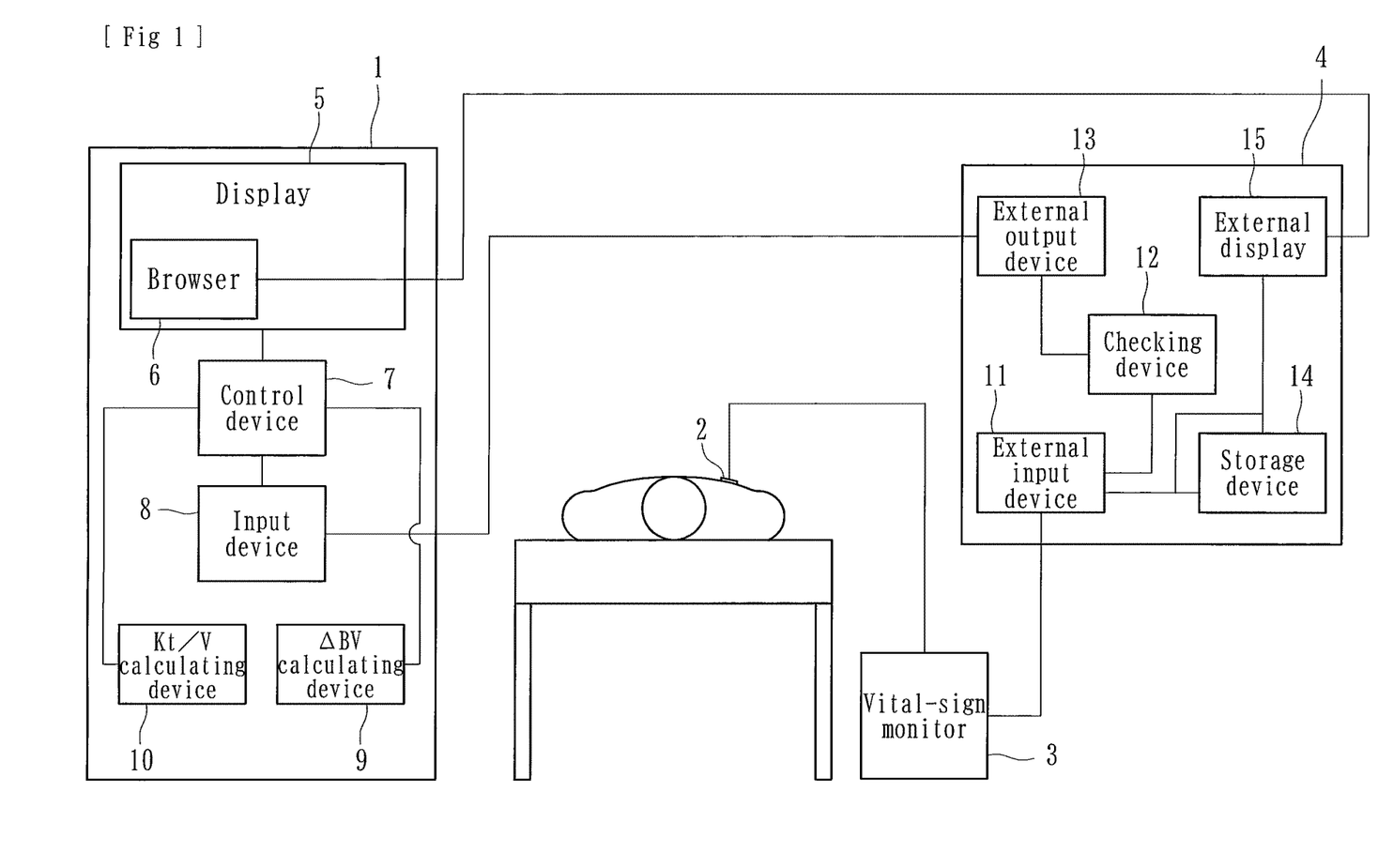
FIG. 1 is a schematic diagram illustrating a blood purification system according to an embodiment of the present invention.

As illustrated in FIG. 1, a blood purification system according to the present embodiment includes a blood purification apparatus 1, a detecting device 2, a vital-sign monitor 3, and an external information-processing apparatus 4. The blood purification apparatus 1 and the external information-processing apparatus 4 are electrically connected to each other, and the external information-processing apparatus 4 and the detecting device 2 are electrically connected to each other, whereby signals are transmittable and receivable thereamong. In the present embodiment, the vital-sign monitor 3 is electrically connected to the external information-processing apparatus 4 and to the detecting device 2. The external information-processing apparatus 4 may include a function corresponding to the vital-sign monitor 3.

Figure 2:
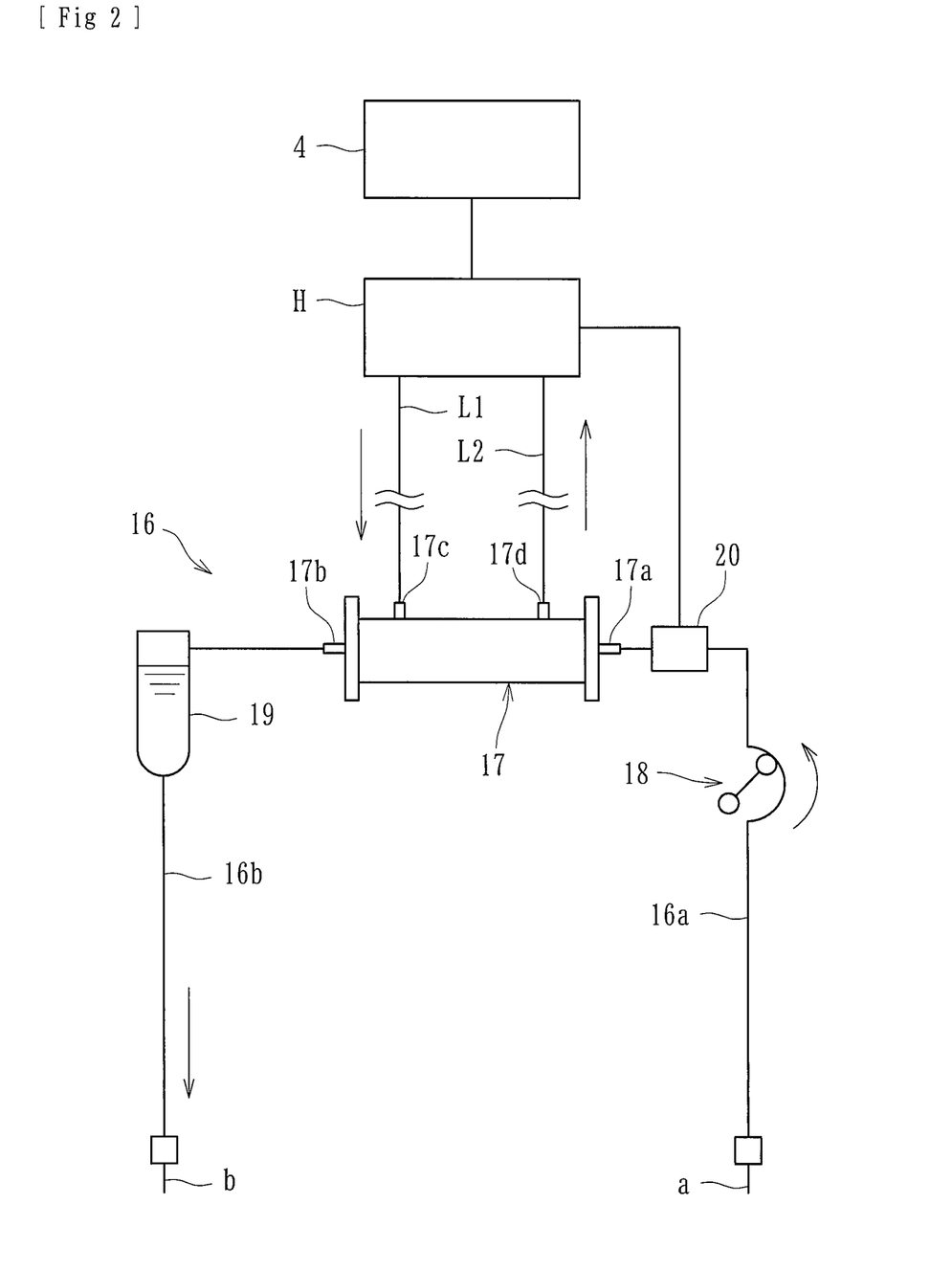
FIG. 2 is a schematic diagram illustrating a blood circuit and a blood purifier included in the blood purification system.
Figure 3:
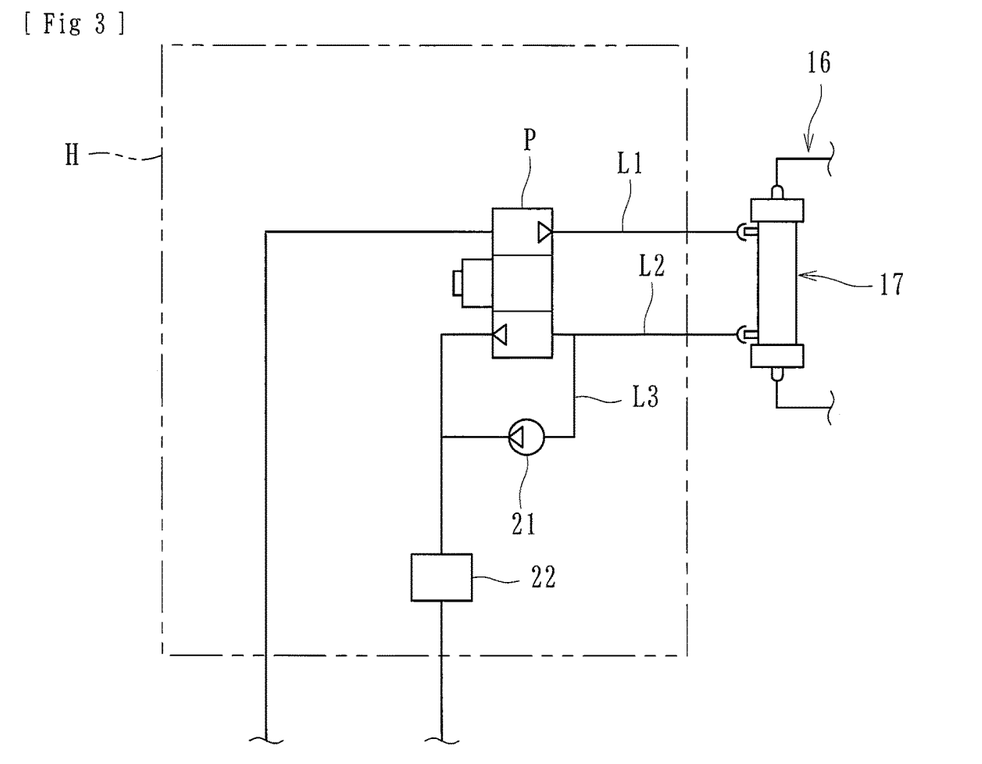
FIG. 3 is a schematic diagram illustrating an internal configuration of a dialysis-apparatus body included in the blood purification system.

The blood purification apparatus 1 according to the present embodiment is a hemodialysis apparatus for performing hemodialysis treatment and ultrafiltration while extracorporeally circulating the blood of a patient and basically includes, as illustrated in FIGS. 2 and 3, a blood circuit 16 for extracorporeally circulating the blood of the patient, a dialyzer 17 as a blood purifier connected to the blood circuit 16 and provided for performing hemodialysis treatment, and a dialysis-apparatus body H connected to the dialyzer 17 and that supplies dialysate while performing ultrafiltration.

The blood circuit 16 is formed of flexible tubes that allow liquid such as blood to flow therethrough and includes an arterial blood circuit 16a and a venous blood circuit 16b. An arterial puncture needle a is connectable to the distal end of the arterial blood circuit 16a. Furthermore, a peristaltic blood pump 18 and a hematocrit sensor 20 are provided at respective halfway positions of the arterial blood circuit 16a. On the other hand, a venous puncture needle b is connectable to the distal end of the venous blood circuit 16b. Furthermore, an air-trap chamber 19 for bubble removal is provided at a halfway position of the venous blood circuit 16b.

The hematocrit sensor 20 includes a light-emitting element such as an LED, and a light-receiving element such as a photodiode. Light at a predetermined wavelength is applied from the light-emitting element to the blood. The light transmitted through or reflected by the blood is received by the light-receiving element. Thus, the hematocrit sensor 20 measures the hematocrit value representing the concentration of the blood of the patient that flows through the blood circuit 16. That is, the hematocrit value is an index representing blood concentration and is specifically expressed as a ratio of the volume of red blood cells to the total volume of blood.

The hematocrit sensor 20 is connected to a ΔBV-calculating device 9 (see FIG. 1) and is capable of calculating the rate of change in the circulating blood volume (ΔBV) on the basis of the hematocrit value detected by the hematocrit sensor 20. Specifically, letting the hematocrit value detected by the hematocrit sensor 20 be Ht, the rate of change in the circulating blood volume ΔBV can be obtained from the following expression: ((Ht at the start of dialysis)−(Ht at a point during the measurement))/(Ht at the point during the measurement)×100. Thus, the rate of change in the volume of circulating blood (ΔBV) of the patient can be detected successively with time elapsed during the dialysis treatment.

When the blood pump 18 is activated with the arterial puncture needle a and the venous puncture needle b stuck in the patient, the blood of the patient flows through the arterial blood circuit 16a and reaches the dialyzer 17, where the blood is purified. Then, while bubbles in the blood are removed in the air-trap chamber 19, the blood flows through the venous blood circuit 16b and returns into the body of the patient. Thus, the blood of the patient can be purified by the dialyzer 17 while being extracorporeally circulated through the blood circuit 16.

The dialyzer 17 has, in a housing thereof, a blood introduction port 17a, a blood delivery port 17b, a dialysate introduction port 17c, and a dialysate delivery port 17d. Among these, the blood introduction port 17a receives the proximal end of the arterial blood circuit 16a, and the blood delivery port 17b receives the proximal end of the venous blood circuit 16b. The dialysate introduction port 17c and the dialysate delivery port 17d are connected to a dialysate introduction line L1 and a dialysate drain line L2, respectively, extending from the dialysis-apparatus body H.

The housing of the dialyzer 17 houses a plurality of hollow fibers. The hollow fibers provide blood channels thereinside, and spaces between the inner peripheral surface of the housing and the outer peripheral surfaces of the hollow fibers serve as dialysate channels. The hollow fibers each have a number of very small holes (pores) extending therethrough from the outer peripheral surface to the inner peripheral surface, thereby forming a hollow fiber membrane. Hence, impurities and the like contained in the blood are allowed to penetrate through the membrane into the dialysate.

As illustrated in FIG. 3, the dialysis-apparatus body H includes a duplex pump P provided over the dialysate introduction line L1 and the dialysate drain line L2, a bypass line L3 connected to the dialysate drain line L2 in such a manner as to bypass the duplex pump P, an ultrafiltration pump 21 connected to the bypass line L3, and a drain-liquid-concentration sensor 22 provided on the dialysate drain line L2. One end of the dialysate introduction line L1 is connected to the dialyzer 17 (the dialysate introduction port 17c), and the other end is connected to a dialysate-supplying device (not illustrated) that prepares a dialysate having a predetermined concentration.

One end of the dialysate drain line L2 is connected to the dialyzer 17 (the dialysate delivery port 17d), and the other end is connected to a drainage device (not illustrated). Hence, the dialysate supplied from the dialysate-supplying device flows through the dialysate introduction line L1, reaches the dialyzer 17, and is delivered to the drainage device through the dialysate drain line L2 and the bypass line L3.

The ultrafiltration pump 21 is provided for removing water from the blood of the patient that flows through the dialyzer 17. Specifically, when the ultrafiltration pump 21 is activated, the amount of liquid discharged from the dialysate drain line L2 becomes larger than the amount of dialysate introduced from the dialysate introduction line L1, and water is removed from the blood by an amount corresponding to the surplus. Note that the removal of water from the blood of the patient may be performed by using another device (for example, a device employing a so-called balancing chamber or the like) instead of the ultrafiltration pump 21.

The drain-liquid-concentration sensor 22 is provided on the dialysate drain line L2 in the dialysis-apparatus body H and is capable of detecting the concentration (for example, the concentrations of substances, such as urea and uric acid, contained in the drain liquid) of the liquid (in the present embodiment, the drain liquid discharged from the dialyzer 17 serving as a blood purifier) generated with the blood purification. The drain-liquid-concentration sensor 22 is connected to a Kt/V-calculating device 10 (see FIG. 1). Hence, the normalized dialysis dose (Kt/V) can be calculated on the basis of changes in the concentration of drain liquid that is detected by the drain-liquid-concentration sensor 22. Thus, the normalized dialysis dose (Kt/V) can be detected successively with time elapsed during the dialysis treatment.

Figure 4:
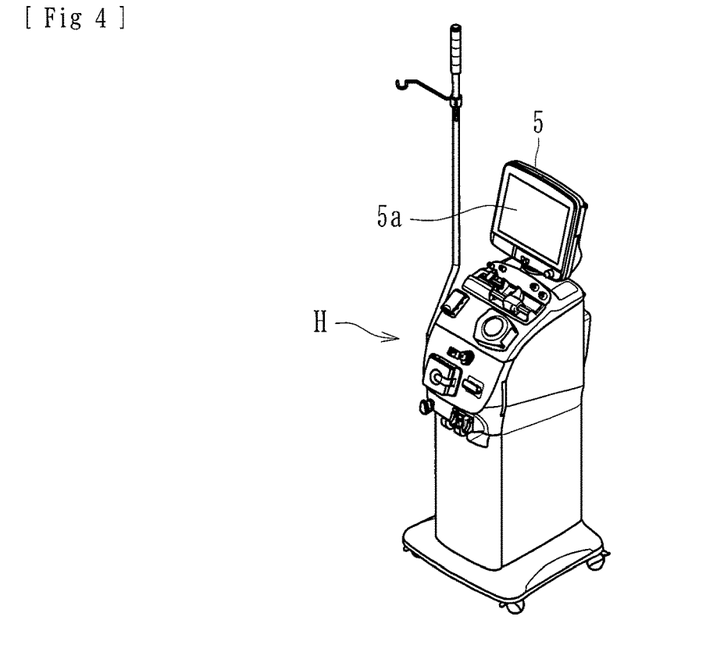
FIG. 4 is an external perspective view of the dialysis-apparatus body included in the blood purification system.
Figure 5:
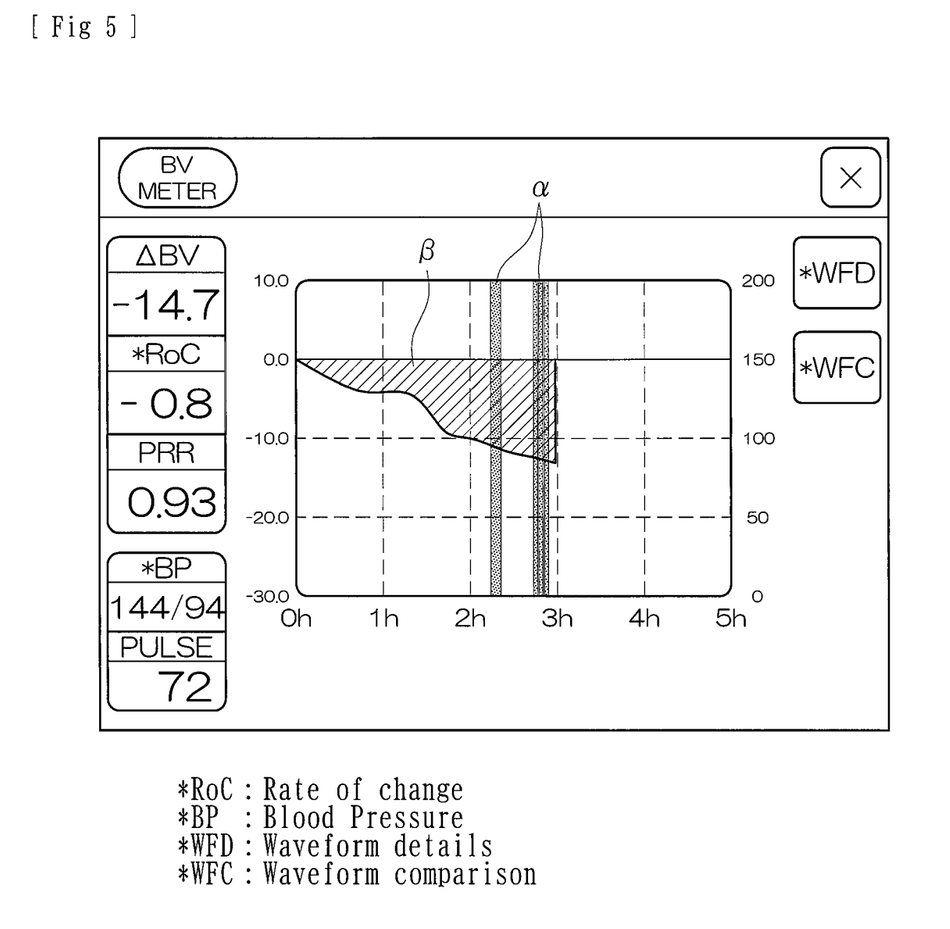
FIG. 5 is a schematic diagram illustrating information (ΔBV and the results of checking) displayed on a screen of a display included in the blood purification system.

As illustrated in FIG. 4, the dialysis-apparatus body H includes a display 5 capable of displaying information on the blood purification treatment in real time. The display 5 includes, for example, a touch-panel liquid-crystal screen 5a on which various pieces of information are displayable. What is to be displayed is controlled by a control device 7 (see FIG. 1). For example, as illustrated in FIG. 5, the liquid-crystal screen 5a of the display 5 displays a time-series chart of ΔBV that is successively calculated by the ΔBV-calculating device 9, and also displays numerical values representing the current ΔBV, the rate of change in ΔBV, and so forth.

An input device 8 is connected to the control device 7 and is electrically connected to an external output device 13 included in the external information-processing apparatus 4. Information (data) outputted from the external output device 13 is inputtable into the input device 8. Hence, information inputted into the input device 8 can be transmitted to the control device 7 and be displayed on the display 5 in the form of charts, numerical values, and the like. The connection between the input device 8 and the external output device 13 may be provided in a wireless manner or the like, as well as in a wired manner.

The detecting device 2 is capable of detecting noninvasive vital signs of the patient during a blood purification treatment in real time and includes, for example, an electrocardiograph, a pulse oximeter, or the like. The detecting device 2 is capable of detecting at least one of the following pieces of information on the patient: electrocardiogram, pulse wave, heart rate (or heartbeat), pulse rate (or pulse), body temperature, oxygen saturation, and respiration rate. Values (vital signs) detected by the detecting device 2 are transmitted to an external input device 11, included in the external information-processing apparatus 4, through the vital-sign monitor 3. The vital-sign monitor 3 is capable of displaying, in real time, values detected by the detecting device 2 in the form of waveforms and numerical values. Herein, the heartbeat refers to the beating of the heart, and the pulse refers to the motion of the artery that occurs when the heart delivers blood to every part of the body. Basically, the heartbeat and the pulse often exhibit the same value. However, extrasystole or arrhythmia may stagger the two.

The term "noninvasive" means that the information is not a parameter obtained by directly measuring the blood. The detecting device 2 may detect any vital signs different from those listed above, as long as such vital signs are real-time noninvasive information. Moreover, the detecting device 2 may have no connection to the vital-sign monitor 3. In that case, the detecting device 2 is directly connected to the external input device 11.

The external information-processing apparatus 4 is capable of receiving and monitoring, in real time, the vital signs detected by the detecting device 2 and includes, as illustrated in FIG. 1, the external input device 11, a checking device 12, the external output device 13, a storage device 14, and an external display 15. The external input device 11 is capable of receiving, in real time, the vital signs detected by the detecting device 2, as described above.

The checking device 12 is electrically connected to the external input device 11 and is capable of checking whether or not the vital signs inputted into the external input device 11 in real time satisfy predetermined conditions. In the present embodiment, the checking device 12 is capable of checking whether or not any of the vital signs inputted in real time is abnormal (for example, whether or not information such as the pulse, the heart rate, or the like of the patient exhibits any abnormal value, or whether or not the waveform of the electrocardiogram indicates arrhythmia or the like).

The external output device 13 is electrically connected to the checking device 12. If it is determined by the checking device 12 that the predetermined conditions are satisfied (in the present embodiment, if any of the vital signs inputted in real time is determined to be abnormal), the external output device 13 outputs the result of the checking or the checked information including the vital signs leading to the result of the checking to the blood purification apparatus 1. That is, in the present embodiment, the result of the checking that is determined to be "abnormal" by the checking device 12 or the checked information including any vital signs leading to the result of the checking is outputted from the external output device 13.

The storage device 14 is electrically connected to the external input device 11 and is capable of memorizing and storing the vital signs (for example, the waveform data and values obtained since the start of the blood purification treatment, the abnormality occurrence history, data on past treatments, and so forth) that are inputted in real time into the external input device 11. The storage device 14 includes a memory, a portable recording medium, or the like that is provided in the external information-processing apparatus 4. Note that the storage device 14 may be omitted. In that case, if there are no abnormalities, the data inputted into the external input device 11 are abandoned.

The external display 15 is electrically connected to the external input device 11 and to the storage device 14 and is capable of displaying the vital signs inputted in real time into the external input device 11 or the vital signs stored in the storage device 14. The external display 15 includes, for example, a liquid-crystal screen and so forth. The blood purification apparatus 1 according to the present embodiment includes a browser 6 that requests (for example, transmits a request signal requesting) the information displayed on the external display 15 and allows such information to be displayed on the display 5 in accordance with the request. The browser 6 is a piece of software through which the screen displayed on the external display 15 is viewable.

In the blood purification system according to the present embodiment, when the checked information (the result of the checking performed by the checking device 12 or the checked information including the vital signs leading to the result of the checking) outputted from the external output device 13 of the external information-processing apparatus 4 is inputted into the input device 8 of the blood purification apparatus 1, the checked information can be displayed on the display 5 of the blood purification apparatus 1. Specifically, when the checked information (the information determined to be "abnormal") is inputted into the input device 8, referring to FIG. 5, the rate of change in the circulating blood volume ΔBV calculated by the ΔBV-calculating device 9 is displayed as a chart β, with a chart α indicating that any checked information is inputted being superposed thereon.

In the chart α, each time period from when any checked information starts to be inputted until when the input of the checked information is ended is represented as a stripe illustrated by changing the background color. The width of the strip in the lateral direction in the drawing corresponds to the duration of the abnormality. In the present embodiment, different background colors are used for different time periods of input of abnormality and for different types of abnormality. Alternatively, the background color may be changed sequentially with the type of abnormality or if any specific "abnormality" occurs repeatedly. In the present embodiment, not only the above charts but also values of "blood pressure" and "pulse" are displayed in one screen. These pieces of information represent the measurement results (the results of intermittent measurements) obtained by a sphygmomanometer (a measuring instrument including a cuff to be wrapped around) included in the blood purification apparatus 1. Hence, such pieces of information are not regarded as "real-time data" and each therefore do not correspond to the "noninvasive vital sign" according to the present invention (the same applies to the cases illustrated in FIGS. 6 and 7).

Figure 6:
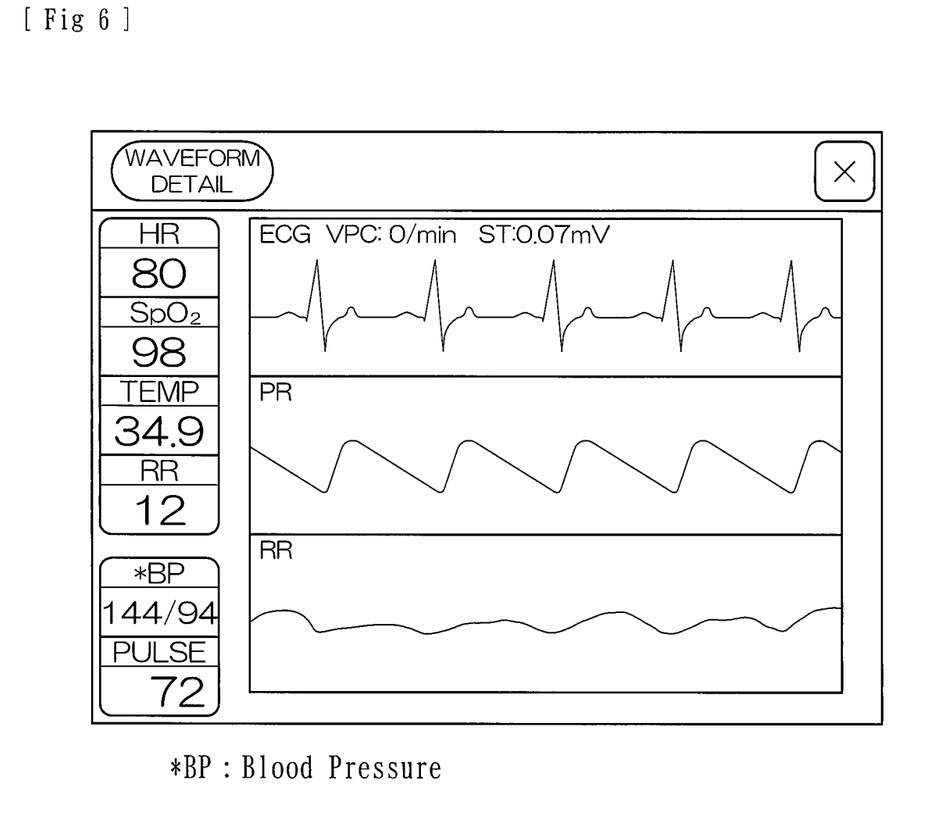
FIG. 6 is another schematic diagram illustrating information (waveform details) displayed on the screen of the display included in the blood purification system.
Figure 7:
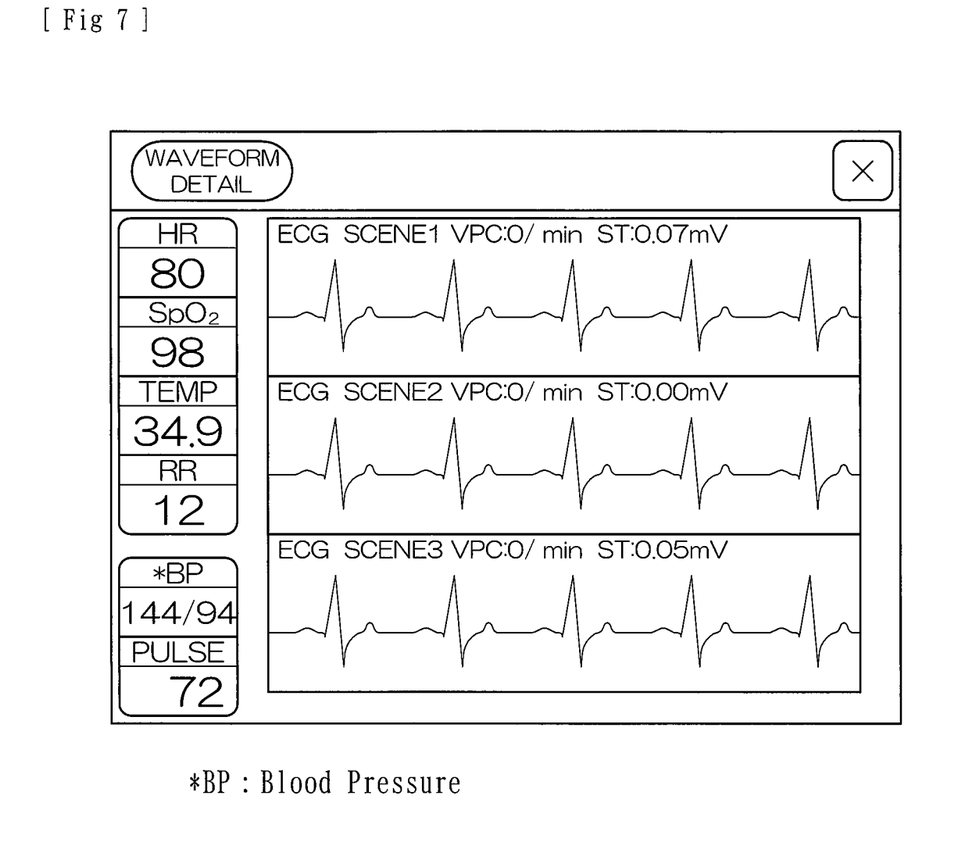
FIG. 7 is yet another schematic diagram illustrating information (waveform comparison) displayed on the screen of the display included in the blood purification system.

Furthermore, when a display item "WFD (WAVEFORM DETAILS)" provided on the screen illustrated in FIG. 5 is touched, a plurality of waveforms representing different kinds of data detected by the detecting device 2 are displayed as illustrated in FIG. 6. In this screen, the current values are displayed on the left side including, for example in order from the top, heart rate (HR), oxygen saturation (SpO2), body temperature (TEMP), and respiration rate (RR). When another display item "WFC (WAVEFORM COMPARISON)" provided on the screen illustrated in FIG. 5 is touched and thus inputted, a plurality of waveforms representing one specific kind of data but obtained in different time periods (in the present embodiment, waveforms of electrocardiogram) are displayed as illustrated in FIG. 7, allowing the comparison of changes in the waveforms observed with time elapsed during the treatment or the trends in the past waveforms. Such pieces of information of "WAVEFORM DETAILS" and "WAVEFORM COMPARISON" obtained by the external information-processing apparatus 4 are viewable on the display 5 through the browser 6.

Figure 9:
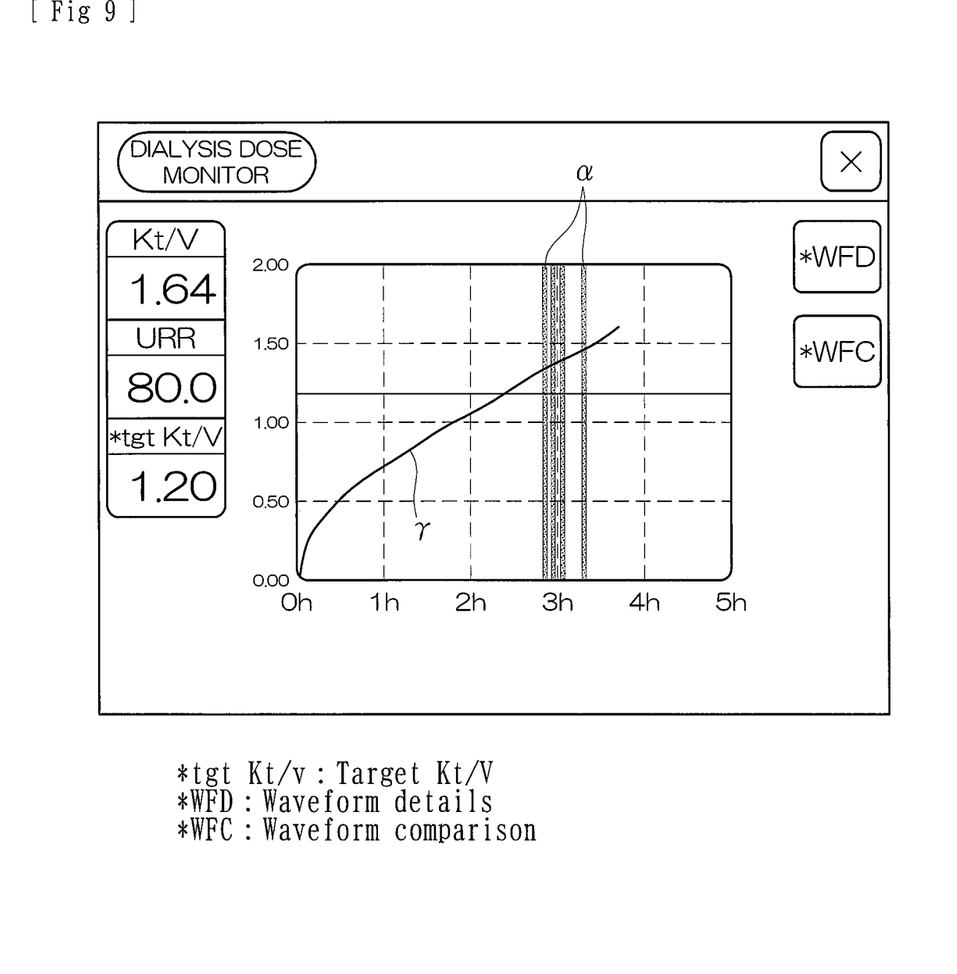
FIG. 9 is yet another schematic diagram illustrating information (Kt/V and the results of checking) displayed on the screen of the display included in the blood purification system.

If any checked information (information determined to be "abnormal") is inputted into the input device 8, referring to FIG. 9, the normalized dialysis dose (Kt/V) calculated by the Kt/V-calculating device 10 is displayed in the form of a chart γ regarding the blood purification treatment. Another chart α indicating that any checked information is inputted may be superposed on the chart γ. The chart α has been described above.

Figure 8:
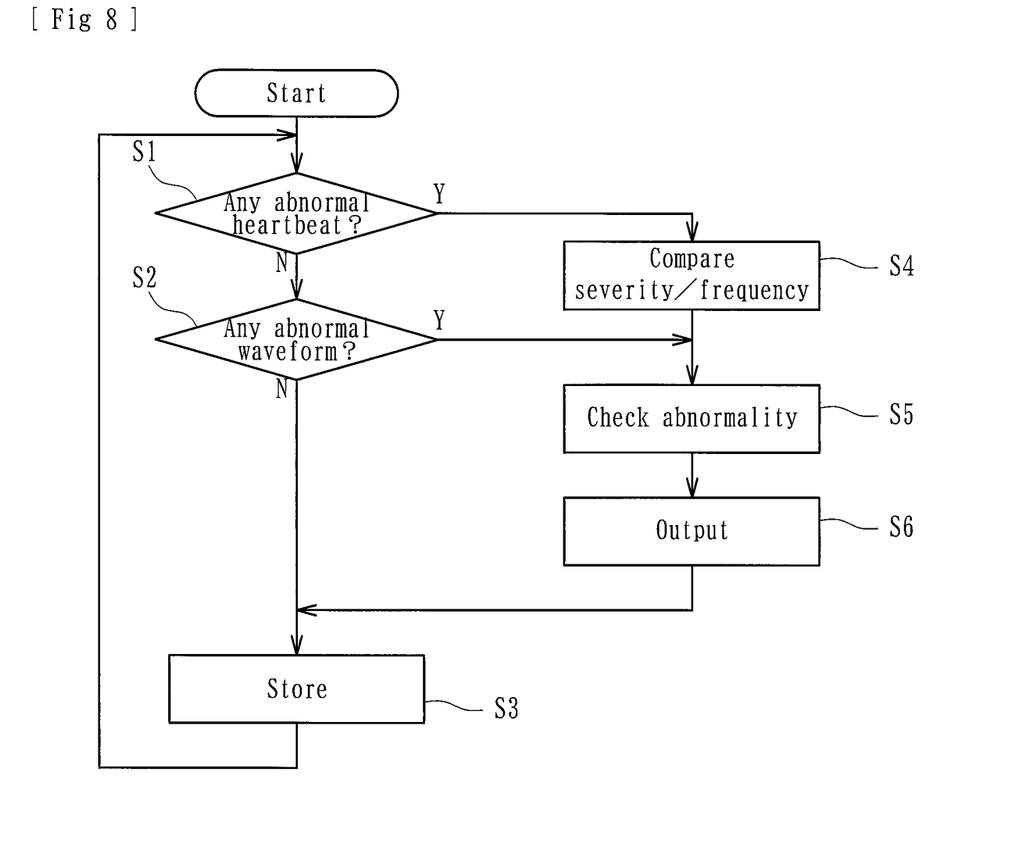
FIG. 8 is a flow chart illustrating a checking process performed by a checking device included in the blood purification system.

Now, a checking method employed by the checking device 12 of the blood purification system according to the present embodiment will be described with reference to a flow chart illustrated in FIG. 8. The flow chart illustrates a process of obtaining a vital sign regarding the electrocardiogram through the detecting device 2. The flow chart is also applicable to processes of obtaining other vital signs.

First in step S1, the presence of arrhythmia or any noise is checked on the basis of the vital sign of the patient inputted into the external input device 11. If it is determined in this step that there is arrhythmia, the arrhythmia is classified on the basis of the severity/frequency in step S4. If it is determined that there is noise, the vital sign is excluded from the items to be checked. Then, the process proceeds to step S2, where it is checked whether or not the waveform has any abnormality. Specifically, it is checked whether or not there are any abnormalities in the QRS complex, the T wave, the ST deflection, and the QT interval.

For example, if the QRS complex is wide, a bundle branch block (a conduction disturbance in the electrocardiograph that occurs at a more distal part than the bundle of His (a bundle of cardiac muscle fibers associated with the pulsation and passing through the wall of the ventricular canal)) or a myocardial infarction is suspected. In particular, a myocardial infarction with an abnormal Q wave is highly suspected. If the T wave is flat or forms a downward peak, a myocardial ischemia is suspected. An ST deflection is a sign of an ischemic heart disease. A downward ST segment is a sign of angina pectoris. An upward ST segment is a sign of a myocardial infarction. Furthermore, if the QT interval representing cardiac excitability is extended, a serious arrhythmia (ventricular fibrillation) tends to occur.

After a general checking of any abnormalities in step S5 on the basis of the information obtained in steps S4 and S2, the result of the checking or the checked information including the vital sign leading to the result of the checking is outputted to the blood purification apparatus 1 (in step S6), and the vital sign inputted in real time and the result of the checking are memorized and stored (in step S3). If no abnormalities are observed in steps S1 and S2, the process proceeds to step S3, where the vital sign inputted in real time is memorized and stored. When the storing in step S3 is complete, the process returns to step S1, and the subsequent steps are performed again. Thus, only if it is determined by the checking device 12 that there are any abnormalities, the result of the checking or the checked information including the vital sign leading to the result of the checking is outputted to the blood purification apparatus 1.

According to the above embodiment, the external information-processing apparatus 4 includes the external input device 11 into which a vital sign detected by the detecting device 2 is inputtable in real time, the checking device 12 capable of checking whether or not the vital sign inputted in real time into the external input device 11 satisfies the predetermined condition, and the external output device 13 capable of outputting, if it is determined by the checking device 12 that the vital sign satisfies the predetermined condition, the result of the checking or the checked information including the vital sign leading to the result of the checking to the blood purification apparatus. The checked information outputted from the external output device 13 is displayable on the display 5 of the blood purification apparatus 1. Therefore, while the manufacturing cost of the blood purification apparatus 1 is suppressed, any changes in the patient's condition can be efficiently and assuredly notified on the basis of noninvasive vital signs of the patient that are observed during the blood purification treatment.

The checking device 12 according to the present embodiment is capable of checking whether or not the vital sign inputted in real time is abnormal. Furthermore, the result of the checking that is determined to be abnormal or the checked information including the vital sign leading to the result of the checking is outputted from the external output device. Therefore, while the manufacturing cost of the blood purification apparatus 1 is suppressed, any abnormalities can be efficiently and assuredly notified on the basis of noninvasive vital signs of the patient that are observed during the blood purification treatment.

The external information-processing apparatus 4 according to the present embodiment includes the storage device 14 capable of memorizing and storing the vital sign inputted in real time into the external input device 11. Therefore, the vital sign that is inputted in real time into the external input device during the treatment can be referred to whenever necessary. The external information-processing apparatus 4 according to the present embodiment further includes the external display 15 capable of displaying the vital sign inputted in real time into the external input device 11. Therefore, information including the vital sign to be displayed can be processed by the external information-processing apparatus 4.

The blood purification apparatus 1 according to the present embodiment includes the browser 6 capable of requesting the information displayed on the external display 15 and that allows the information to be displayed on the display 5 in accordance with the request. Therefore, the blood purification apparatus 1 does not need to perform arithmetic processes and the like that are necessary for displaying the vital sign in real time. The noninvasive vital sign detectable by the detecting device 2 includes at least one of the electrocardiogram, pulse wave, heart rate, pulse rate, body temperature, oxygen saturation, and respiration rate of the patient. Therefore, changes in the patient's condition can be efficiently and assuredly notified on the basis of any of the electrocardiogram, pulse wave, heart rate, pulse rate, body temperature, oxygen saturation, and respiration rate of the patient.

The external information-processing apparatus 4 may be a central monitoring apparatus capable of transmitting conditions for or information on the blood purification treatment to the blood purification apparatus 1 or a bed-side terminal (for example, a bed-side monitor or the like) provided near the patient during the blood purification treatment. If the external information-processing apparatus 4 is a central monitoring apparatus or a bed-side terminal, any central monitoring apparatus or any bed-side terminal included in any known blood purification system can be used. Alternatively, any abnormal signals generated in the external information-processing apparatus 4 (a bed-side terminal such as a bed-side monitor) may be eventually inputted to the blood purification apparatus 1 via a central monitoring apparatus.

While the present embodiment has been described above, the present invention is not limited thereto. For example, the checking device 12 is not limited to a device that checks whether or not the vital sign inputted in real time is abnormal. The checking device 12 only needs to be capable of checking whether or not the vital sign inputted in real time into the external input device 11 satisfies the predetermined condition (for example, a predetermined condition that is not abnormal but is highly expected to become abnormal with the elapse of time). The blood purification apparatus according to the present embodiment is applied to a hemodialysis apparatus for giving hemodialysis treatment but may alternatively be applied to a blood purification apparatus for giving blood purification treatment of any other type.

The present invention is applicable to any blood purification system having a different appearance, additional functions, and so forth, as long as the external information-processing apparatus includes an external input device into which a vital sign detected by a detecting device is inputtable in real time, a checking device capable of checking whether or not the vital sign inputted in real time into the external input device satisfies a predetermined condition, and an external output device capable of outputting, if it is determined by the checking device that the vital sign satisfies the predetermined condition, the result of the checking or the checked information including the vital sign leading to the result of the checking to the blood purification apparatus, and the checked information outputted from the external output device is displayable on a display included in the blood purification apparatus.

REFERENCE SIGN LIST

1 blood purification apparatus
2 detecting device
3 vital-sign monitor
4 external information-processing apparatus
5 display
6 browser
7 control device
8 input device
9 ΔBV-calculating device
10 Kt/V-calculating device
11 external input device
12 checking device
13 external output device
14 storage device
15 external display
16 blood circuit
17 dialyzer
18 blood pump
19 air-trap chamber
20 hematocrit sensor
21 ultrafiltration pump
22 drain-liquid-concentration sensor

The invention claimed is:

1. A blood purification system comprising:
   A. a blood purification apparatus capable of performing blood purification treatment in which blood of a patient that is extracorporeally circulated is purified, the blood purification apparatus includes:
      i. a display capable of displaying information on the blood purification treatment in real time;
   B. a detecting device that detects in real time a noninvasive vital sign of the patient during the blood purification treatment; and
   C. an external information-processing apparatus that receives and monitors in real time the vital sign detected by the detecting device, the external information-processing apparatus being configured to be electrically connected to a vital sign monitor;
   the external information-processing apparatus includes:
      i. an external input device into which the vital sign detected by the detecting device is inputtable in real time;
      ii. a checking device that determines whether or not the vital sign inputted in real time into the external input device satisfies a predetermined condition;
      iii an external output device that outputs, if it is determined by the checking device that the vital sign satisfies the predetermined condition, a result of the checking or checked information including the vital sign leading to the result of the checking to the blood purification apparatus,
   wherein the checked information outputted from the external output device is displayable on the display included in the blood purification apparatus; and
   wherein the external output device only outputs the vital sign if the checking device determines the vital sign inputted in real time is abnormal and free of external noise distorting the vital sign.

2. The blood purification system according to claim 1, wherein the result of the checking that is determined to be abnormal or the checked information including the vital sign leading to the result of the checking is outputted from the external output device.

3. The blood purification system according to claim 1, wherein the external information-processing apparatus includes a storage device capable of memorizing and storing the vital sign inputted in real time into the external input device.

4. The blood purification system according to claim 1, wherein the external information-processing apparatus includes an external display capable of displaying the vital sign inputted in real time into the external input device, and wherein the external display and the display are separate.

5. The blood purification system according to claim 1, wherein the blood purification apparatus includes a browser capable of requesting information displayed on the external display and that allows the information to be displayed on the display in accordance with the request.

6. The blood purification system according to claim 1, wherein the noninvasive vital sign detectable by the detecting device includes at least one of electrocardiogram, pulse wave, heart rate, pulse rate, body temperature, oxygen saturation, and respiration rate of the patient.

7. The blood purification system according to claim 1, wherein the external information-processing apparatus is a central monitoring apparatus capable of transmitting a condition for or information on the blood purification treatment to the blood purification apparatus or a bed-side terminal provided near the patient during the blood purification treatment.

8. The blood purification system according to claim 2, wherein the external information-processing apparatus includes a storage device capable of memorizing and storing the vital sign inputted in real time into the external input device.

9. The blood purification system according to claim 2, wherein the external information-processing apparatus includes an external display capable of displaying the vital sign inputted in real time into the external input device.

10. The blood purification system according to claim 3, wherein the external information-processing apparatus includes an external display capable of displaying the vital sign inputted in real time into the external input device, and the blood purification apparatus includes a browser capable of requesting information displayed on the external display and that allows the information to be displayed on the display in accordance with the request.

11. The blood purification system according to claim 4, wherein the blood purification apparatus includes a browser capable of requesting information displayed on the external display and that allows the information to be displayed on the display in accordance with the request.

12. The blood purification system according to claim 5, wherein the noninvasive vital sign detectable by the detecting device includes at least one of electrocardiogram, pulse wave, heart rate, pulse rate, body temperature, oxygen saturation, and respiration rate of the patient.

13. The blood purification system according to claim 6, wherein the external information-processing apparatus is a central monitoring apparatus capable of transmitting a condition for or information on the blood purification treatment to the blood purification apparatus or a bed-side terminal provided near the patient during the blood purification treatment.

14. The blood purification system according to claim 1, wherein the blood purification system includes the vital-sign monitor and the vital-sign monitor displays, in real time, values detected by the detecting device, and the display is in a form of waveforms and numerical values.

15. The blood purification system according to claim 1, wherein the blood purification system includes the vital-sign monitor and the vital-sign monitor is connected to the detecting device.

16. The blood purification system according to claim 1, wherein the blood purification system includes the vital-sign monitor and the vital-sign monitor is free of connection to the detecting device and the detecting device is directly connected to the external input device.

17. The blood purification system according to claim 1, wherein the blood purification apparatus includes a ΔBV-calculating device that calculates a rate of change of a blood volume circulating based upon a detected hematocrit value.

18. The blood purification system according to claim 17, wherein the blood purification system includes a hemocrit sensor and the hemocrit sensor provides the detected hemocrit value to the ΔBV-calculating device so that the ΔBV-calculating device calculates the rate of change in the blood volume-circulating based upon the detected hemocrit value.

19. The blood purification system according to claim 1, wherein the blood purification apparatus includes a Kt/V-calculating device to calculate a normalized dialysis dose.

20. The blood purification system according to claim 19, wherein the blood purification system includes a drain-liquid-concentration sensor that is connected to the Kt/V-calculating device so that the normalized dialysis dose is calculated on a basis of change in a concentration of drain liquid that is detected by the drain-liquid-concentration sensor.

* * * * *